United States Patent

Bicker et al.

[11] 4,083,987
[45] Apr. 11, 1978

[54] 4-IMINO-1,3-DIAZABICYCLO-(3.1.0)-HEXAN-2-ONE AS A CANCEROSTAT AND IMMUNO-STIMULANT

[75] Inventors: Uwe Bicker, Mannheim; Wolfgang Kampe, Heddesheim; Wolfgang Steingross, Viernheim, all of Germany

[73] Assignee: Boehringer Mannheim GmbH, Mannheim-Waldhof, Germany

[21] Appl. No.: 690,340

[22] Filed: May 26, 1976

[30] Foreign Application Priority Data

Jul. 8, 1975 Germany .............................. 2530398

[51] Int. Cl.² ................ C07D 487/04; A61K 31/415
[52] U.S. Cl. .................................. 424/273 R; 548/302
[58] Field of Search .......................... 260/309.6, 309.7; 424/273; 548/302

[56] References Cited

PUBLICATIONS

Hillers et al. Chem. Abst. 1972, vol. 76, No. 126,824j.

*Primary Examiner*—Natalie Trousof
*Attorney, Agent, or Firm*—Burgess, Dinklage & Sprung

[57] ABSTRACT

4-Imino-1,3-diazabicyclo[3.1.0]-hexan-2-one of one or more of the tautomeric formulas

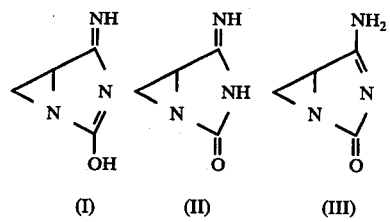

or a physiologically compatible salt thereof exhibits cancerostatic and immuno-stimulant activity. It is produced by cyclized 1-carboxamido-2-cyanoaziridine in an anhydrous polar organic solvent in the presence of a catalytic amount of an alkali.

7 Claims, No Drawings

4-IMINO-1,3-DIAZABICYCLO-(3.1.0)-HEXAN-2-ONE AS A CANCEROSTAT AND IMMUNO-STIMULANT

The present invention is concerned with a new substance which is cancerostatic and has an immunity-stimulating action and is also concerned with the preparation thereof.

A number of cancerostatically-acting substances is already known which, by means of their attack in the metabolism of the very rapidly dividing cancer cells, so strongly damage the tumors that the growth thereof is reduced or even a regression is achieved. However, a complete regression only by medication is very difficult to achieve since, in the case of the necessarily high dosages, healthy body tissues are also attacked and destroyed. On the other hand, it has been found that most cytostatic compounds, at the necessarily high dosages, damage the body's inherent immune defense mechanism so that this is no longer able to destroy the remaining cancer cells or to prevent a further growth thereof. In addition, due to the reduction of the immune defense mechanism, the susceptibility of the already weakened body to bacterial or viral infections is increased.

Consequently, there is a great need for a cancerostatically-effective therapeutic substance which does not impair the body's inherent immune mechanism or which stimulates it.

We have now found that 4-imino-1,3-diazabicyclo-[3.1.0]hexan-2-one and the physiologically compatible salts thereof possess the desired cancerostatic and immunity-stimulating properties. This compound can be represented by the following tautomeric structural formulae:

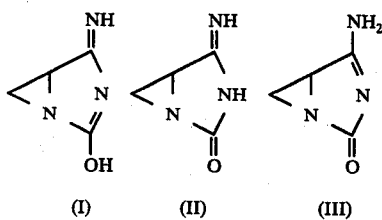

(I)     (II)     (III)

However, it is not certain whether the compound itself or a metabolite thereof formed in the body represents the actual active principle.

We have found that 1-carboxamido-2-cyanoaziridine, which is described in German Democratic Republic Pat. No. 110,492, can be cyclized in a substantially anhydrous, polar, organic solvent, preferably in an alcohol containing up to 4 carbon atoms, with the addition of a catalytic amount of an alkali to give the above new compound, which crystallizes readily, is stable in dry form and is very readily soluble in water, physiological saline and aqueous alkali metal hydroxide solutions.

The structure of the new compound has not been finally elucidated but the physico-chemical investigations (analysis, mass spectrum, infra-red spectrum and NMR spectrum) which have been carried out with the compound indicate one of the above structures (I), (II) or (III). The good water solubility, as well as the decomposition point of the substance of over 250° C. indicate ionic exchange actions and thus also the above-described tautomeric structures.

The following Example illustrates the preparation of the new compound according to the present invention:-

EXAMPLE

4-Imino-1,3-diazabicyclo[3.1.0]hexan-2-one 1.1 g (10 mMol) 1-carboxamido-2-cyanoaziridino is dissolved in 5 ml anhydrous methanol. 56 mg (1 mMol) potassium hydroxide in 5 ml anhydrous methanol are added dropwise at 50° C with the exclusion of moisture. Within the course of a few minutes, 0.66 g (6 mMol) 4-imino-1,3-diazabicyclo[3.1.0]hexan-2-one precipitate out, corresponding to a yield of 60% theory. After recrystallization from anhydrous methanol, the compound has a decomposition point of more than 250° C.

The infra-red spectrum of the compound in potassium bromide shows two wide bands between 3300 to 2500 $cm^{-1}$ and 1800 to 1400 $cm^{-1}$, sharper bands, for example, at 1295 $cm^{-1}$, 1232 $cm^{-1}$, 1178 $cm^{-1}$, 1013 $cm^{-1}$, 922 $cm^{-1}$, 855 $cm^{-1}$, 820 $cm^{-1}$, 682 $cm^{-1}$ and 542 $cm^{-1}$.

The mass spectrum shows a mol peak at 111, as well as peaks at 110, 83, 68 and 41.

The NMR spectrum (deuterodimethyl formamide) shows the following bands;

| chemical displacement against TMS in ppm | coupling constants in $H_2$ |
|---|---|
| V (1) = 2.23 | J (1.2) 0.5 |
| V (2) = 2.51 | J (1.3) 2.93 |
| V (3) = 3.47 | J (2.3) 5.27 |

Microelementary analysis gives the following values:

| $C_4H_5ON_3$ | | | |
|---|---|---|---|
| calc. : | C 43.24%; | H 4.53%; | N 37.82% |
| found : | 42.62%; | 4.03%; | 37.52% |

The pharmacological properties of the new compound were determined as follows:

1. Cancerostatic Effectiveness

Sprague-Dawley rats with a body weight of 80 to 120 g and an age of 6 to 8 weeks were subcutaneously inoculated in the neck with tumor cells. In each case, there was used 0.1 ml of an aqueous suspension of about $10^6$ tumor cells of the Walker sarcoma 256 (solid, rat).

4-Imino-1,3-diazabicyclo[3.1.0]hexan-2-one was dissolved in physiological saline solution (in each case, the desired amount in 5 ml solution/kg body weight of experimental animal). 6 Hours after inoculation of the animals, these solutions were administered intravenously or orally by means of a stomach tube. The control animals received 5 ml/kg body weight of physiological saline. 20 experimental animals and 20 control animals were used per experiment. The animals were sacrificed with ether after 10 days, the tumors extirpated and the weight of the tumors of the control group compared with those of the experimental group.

The following Table shows that the tumor growth is significantly inhibited in the case of intravenous and oral administration of the substance.

TABLE 1

Inhibition of the growth of Walker sarcoma 256 after a single administraton of 4-imino-1,3-diazabicyclo[3.1.0]-hexan-2-one to Sprague-Dawley rats

| administration route | amount mg./kg. | % inhibition |
| --- | --- | --- |
| intravenous | 0.1 | 7.5 |
| | 1.0 | 17.5 |
| | 10.0 | 49.5 |
| | 100.0 | 31.0 |
| | 200.0 | 39.5 |
| oral | 5.0 | 20.0 |
| | 125.0 | 62.0 |

2. Immunity-stimulating Action

The active material, dissolved in 5 ml physiological saline, was administered intravenously into a vein in the tails of 8 Sprague-Dawley rats with an average body weight of 200 to 250 g. As controls, there were used 8 rats which were only treated with 5 ml physiological saline per kg. body weight. In the following days, 1 to 2 drops of blood were taken from a tail vein and the corpuscular blood components determined. The average values were determined statistically from the 8 values of the individual animals.

It was found that the number of leukocytes increased considerably and also that the percentage proportion of the lymphocytes increased. Only after the expiry of 20 to 25 days were the values of the control animals again reached. On the other hand, the number of erythrocytes did not change significantly over the whole of the experimental period. The experimental results of the third day, which correspond approximately to the maximum increase, are summarized in the following Table 2:

TABLE 2

Increase of the leukocytes after a single intravenous administration of 4-imino-1,3-diazobicyclo[3.1.0]hexan-2-one to Sprague-Dawley rats on the third day after administration

| mg. active material/kg. rat | number of leukocytes/mm$^3$ |
| --- | --- |
| 0 | 7,300 |
| 2 | 10,300 |
| 5 | 9,800 |
| 10 | 10,800 |
| 20 | 12,300 |
| 40 | 10,800 |
| 75 | 11,800 |
| 150 | 8,000 |
| 400 | 6,500 |

Furthermore, the number of antibody-forming spleen cells was determined by Jerne's method (Jerne et al., Science, 140, 405/1963).

20 male white mice with a body weight of 20 to 25 g were each immunized with 1 ml preserved sheep erythrocytes (1 ml contains 5 × 10$^8$ erythrocytes). On the same day, 4-imino-1,3-diazabicyclo[3.1.0]hexan-2-one or a comparative active material, dissolved in 5 ml physiological saline/kg. mouse body weight, were administered intravenously. For control purposes, 20 animals were also immunized with 1 ml sheep erythrocytes and treated with 5 ml/kg physiological saline. Three days after administration, the spleens of the animals were removed under sterile conditions and the number of antibody-forming spleen cells determined according to Jerne's technique. The individual values were determined. The individual results are summarized in the following Table 3:

TABLE 3

Average values of the antibody-forming spleen cells after intravenous administration of various active materials

| active material | amount mg/kg | number of spleen cells | % of the control |
| --- | --- | --- | --- |
| control | — | 4,600 | 100 |
| 4-imino-1,3-diazabicyclo[3.1.0]hexan-2-one | 2.5 | 23,000 | 500 |
| phytohaemagglutinin | 500.0 | 1,400 | 30 |
| cyclophosphamide | 125.0 | 460 | 10 |

From the above experiments, it can be deduced that for the desired pharmacological effect of immunity stimulation, a dosage of about 1 to 50 mg/kg body weight is necessary, which can be administered either all at once or in several individual doses. Since the effect slowly decreases after about 2 weeks, a further treatment can possibly be necessary.

The acute toxicity (LD$_{50}$) in the case of a single intravenous dose was ascertained to be 660 mg/kg in the case of rats and 750 mg/kg in the case of mice. The LD$_{50}$ in the case of oral administration was found to be more than 4.0 mg/kg in the case of mice.

The present invention also provides pharmaceutical composition comprising the new compound and/or at least one physiologically compatible salt thereof, in admixture with a solid or liquid pharmaceutical diluent or carrier.

For the preparation of pharmaceutical compositions, 4-imino-1,3-diazabicyclo[3.1.0]hexan-2-one and/or at least one pharmacologically compatible salt thereof is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatine, agar-agar, calcium phosphate, magnesium stearate animal and vegetable fats and solid high molecular weight polymers (such as polyethylene glycols). Compositions suitable for oral administration can, if desired, contain flavoring and/or sweetening materials.

However, the active material is preferably injected. As injection medium, it is preferred to use water which contains the additives usual in the case of injection solutions, such as stabilizing agents, solubilizing agents and/or weakly alkaline buffers. Additives of this type include, for example, phosphate and carbonate buffers, ethanol, complex-forming agents (for example ethylenediamine-tetraacetic acid and the non-toxic salts thereof) and high molecular weight polymers (for example liquid polyethylene oxide) for viscosity regulation.

When administered in the form of a salt, any physiologically compatible anion can be used, e.g. acetate, citrate, lactate, chloride, bromide, sulfate, phosphate, sulfonates, and the like. These salts can be made by mixing the active compound with aqueous acid.

In the preparation of the active material polar solvents other than methanol can be employed in amount sufficient to dissolved the starting material and end product, e.g. other lower alkanols, dioxane, dimethylsulfoxide, dimethylformamide. Heat is desirable to speed up the isomerization. In place of potassium hydroxide, there can be used other soluble alkalis, e.g. hydroxides and/or carbonates of sodium, lithium, and even strong quaternary ammonium bases. The basic catalyst can be used in as little as about 1 mole % but about 10 mole % is suitable and more can be used, although not necessary.

For treatment of humans the active material may be applied one or more times with each dose containing about 25 to 3000 and preferably about 50 to 500 mg of active material.

It will be appreciated that the instant specification and examples are set forth by way of illustration and not limitation, and that various modifications and changes may be made without departing from the spirit and scope of the present invention.

What is claimed is:

1. 4-Imino-1,3-diazabicyclo[3.1.0]-hexan-2-one or a physiologically compatible salt thereof.

2. A process for the preparation of 4-imino-1,3-diazabicyclo-[3.1.0]-hexan-2-one according to claim 1, comprising contacting 1-carboxamido-2-cyanoaziridine with a catalytic amount of an alkali in a substantially anhydrous polar solvent, whereby the aziridine cyclizes.

3. The process according to claim 2, wherein the solvent used is an anhydrous alcohol containing up to 4 carbon atoms.

4. The process according to claim 3, wherein the alkali is potassium hydroxide and the solvent is heated.

5. An immuno-stimulant composition containing an immuno-stimulant effective amount of 4-imino-1,3-diazabicyclo[3.1.0]-hexan-2-one or a physiologically compatible salt thereof according to claim 1 in admixture with a physiologically compatible diluent.

6. A unit dose of a composition according to claim 5 containing about 25 to 3000 mg of active material.

7. A method of stimulating an immune response in a patient which comprises administering to the patient an immuno-stimulant effective amount of 4-imino-1,3-diazabicyclo[3.1.0]-hexan-2-one or a physiologically compatible salt thereof according to claim 1.

* * * * *